US012727825B2

(12) United States Patent
An et al.

(10) Patent No.: US 12,727,825 B2
(45) Date of Patent: Sep. 8, 2026

(54) SYSTEMS AND METHODS FOR PATIENT MONITORING

(71) Applicant: Cardiac Pacemakers, Inc., St. Paul, MN (US)

(72) Inventors: Qi An, Shoreview, MN (US); Jeffrey E. Stahmann, Ramsey, MN (US); Pramodsingh Hirasingh Thakur, Woodbury, MN (US); Viktoria A. Averina, Shoreview, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 245 days.

(21) Appl. No.: 18/755,947

(22) Filed: Jun. 27, 2024

(65) Prior Publication Data

US 2024/0341689 A1 Oct. 17, 2024

Related U.S. Application Data

(63) Continuation of application No. 17/697,133, filed on Mar. 17, 2022, now Pat. No. 12,102,448, which is a (Continued)

(51) Int. Cl.

*A61B 5/00* (2006.01)
*A61B 5/02* (2006.01)
(Continued)

(52) U.S. Cl.

CPC ............ *A61B 5/686* (2013.01); *A61B 5/0031* (2013.01); *A61B 5/02028* (2013.01); (Continued)

(58) Field of Classification Search

CPC ... A61B 5/686; A61B 5/0031; A61B 5/02028; A61B 5/0205; A61B 5/201; (Continued)

(56) References Cited

U.S. PATENT DOCUMENTS 7,927,284 B2 4/2011 Dalal et al.
8,052,611 B2 11/2011 Wariar et al.
(Continued)

FOREIGN PATENT DOCUMENTS

CN 103212063 B1 7/2015
CN 104838382 A 8/2015
(Continued)

OTHER PUBLICATIONS

U.S. Appl. No. 15/422,789 U.S. Pat. No. 11,298,081, filed Feb. 2, 2017, Systems and Methods for Patient Monitoring.
(Continued)

*Primary Examiner* — Eugene T Wu
(74) *Attorney, Agent, or Firm* — Nelson Mullins Riley & Scarborough LLP

(57) ABSTRACT

Systems and methods for monitoring patients with a chronic disease such as heart failure are disclosed. The system may include a physiological sensor circuit to sense physiological signals and generate signal metrics from the physiological signals. The system may include a health status analyzer circuit to use the signal metrics to generate one or more stability indicators of patient health status, such as stability of heart failure status. The system may additionally generate one or more health status indicators indicating patient health status such as heart failure progression. A patient disposition decision may be generated using the health status indicators and the stability indicators to provide an indication of readiness for patient discharge from or a risk of admission to a hospital.

20 Claims, 5 Drawing Sheets

Related U.S. Application Data continuation of application No. 15/422,789, filed on Feb. 2, 2017, now Pat. No. 11,298,081.

(60) Provisional application No. 62/294,555, filed on Feb. 12, 2016.

(51) Int. Cl.

| | |
|---|---|
| ***A61B 5/0205*** | (2006.01) |
| ***A61B 5/20*** | (2006.01) |
| ***G16H 20/10*** | (2018.01) |
| ***G16H 20/30*** | (2018.01) |
| ***G16H 40/63*** | (2018.01) |
| ***G16H 50/30*** | (2018.01) |
| ***G16H 50/70*** | (2018.01) |
| *A61B 5/08* | (2006.01) |

(52) U.S. Cl.

CPC ............ *A61B 5/0205* (2013.01); *A61B 5/201* (2013.01); *A61B 5/4836* (2013.01); *A61B 5/7225* (2013.01); *A61B 5/725* (2013.01); *A61B 5/7275* (2013.01); *G16H 20/10* (2018.01); *G16H 20/30* (2018.01); *G16H 40/63* (2018.01); *G16H 50/30* (2018.01); *G16H 50/70* (2018.01); *A61B 5/08* (2013.01)

(58) Field of Classification Search

CPC ..... A61B 5/4836; A61B 5/7225; A61B 5/725; A61B 5/7275; A61B 5/08; G16H 20/10; G16H 20/30; G16H 40/63; G16H 50/30; G16H 50/70

See application file for complete search history.

(56) References Cited

U.S. PATENT DOCUMENTS

| | | | |
|---|---|---|---|
| 8,751,257 B2 | 6/2014 | Amland et al. | |
| 11,298,081 B2 | 4/2022 | An et al. | |
| 2008/0228090 A1 | 9/2008 | Wariar et al. | |
| 2012/0253207 A1 | 10/2012 | Sarkar et al. | |
| 2012/0296671 A1 | 11/2012 | Simons-Nikolova et al. | |
| 2013/0030312 A1 | 1/2013 | Keel et al. | |
| 2013/0116578 A1 | 5/2013 | An et al. | |
| 2014/0276164 A1 | 9/2014 | Thakur et al. | |
| 2014/0343438 A1* | 11/2014 | Sweeney .............. | A61B 5/7275 600/483 |
| 2015/0186607 A1 | 7/2015 | Geleijnse et al. | |
| 2015/0213225 A1 | 7/2015 | Amarasingham et al. | |
| 2015/0261924 A1 | 9/2015 | Geleijnse et al. | |
| 2015/0297078 A1 | 10/2015 | Gross et al. | |
| 2015/0305688 A1 | 10/2015 | Rath et al. | |
| 2015/0342540 A1 | 12/2015 | An et al. | |
| 2017/0231568 A1 | 8/2017 | An et al. | |
| 2022/0202364 A1 | 6/2022 | An et al. | |

FOREIGN PATENT DOCUMENTS

| | | |
|---|---|---|
| CN | 105228513 A | 1/2016 |
| CN | 108697330 A | 10/2018 |
| CN | 108697330 B | 7/2022 |
| EP | 3413783 A1 | 12/2018 |
| WO | WO-2008002525 A2 | 1/2008 |
| WO | WO-2012057860 A1 | 5/2012 |
| WO | WO-2 452 619 B1 | 10/2013 |
| WO | WO-2015023971 A1 | 2/2015 |
| WO | WO-2015175207 A1 | 11/2015 |
| WO | WO-2017139164 A1 | 8/2017 |

OTHER PUBLICATIONS

U.S. Appl. No. 17/697,133, filed Mar. 17, 2022, Systems and Methods for Patient Monitoring.

"U.S. Appl. No. 15/422,789, 312 Amendment filed Jan. 27, 2022", 8 pgs.

"U.S. Appl. No. 15/422,789, Advisory Action mailed Mar. 9, 2021", 2 pgs.

"U.S. Appl. No. 15/422,789, Examiner Interview Summary mailed Feb. 17, 2021", 3 pgs.

"U.S. Appl. No. 15/422,789, Final Office Action mailed Jan. 24, 2020", 14 pgs.

"U.S. Appl. No. 15/422,789, Final Office Action mailed Oct. 5, 2021", 5 pgs.

"U.S. Appl. No. 15/422,789, Final Office Action mailed Dec. 31, 2020", 12 pgs.

"U.S. Appl. No. 15/422,789, Non Final Office Action mailed Apr. 12, 2021", 7 pgs.

"U.S. Appl. No. 15/422,789, Non Final Office Action mailed May 14, 2020", 13 pgs.

"U.S. Appl. No. 15/422,789, Non Final Office Action mailed Sep. 18, 2019", 13 pgs.

"U.S. Appl. No. 15/422,789, Notice of Allowance mailed Dec. 8, 2021", 7 pgs.

"U.S. Appl. No. 15/422,789, PTO Response to Rule 312 Communication mailed Feb. 9, 2022", 2 pgs.

"U.S. Appl. No. 15/422,789, Response filed Mar. 1, 2021 to Final Office Action mailed Dec. 31, 2020", 13 pgs.

"U.S. Appl. No. 15/422,789, Response filed Mar. 23, 2020 to Final Office Action mailed Jan. 24, 2020", 13 pgs.

"U.S. Appl. No. 15/422,789, Response filed Jul. 12, 2021 to Non Final Office Action mailed Apr. 12, 2021", 10 pgs.

"U.S. Appl. No. 15/422,789, Response filed Aug. 14, 2020 to Non Final Office Action mailed May 14, 2020", 10 pgs.

"U.S. Appl. No. 15/422,789, Response filed Nov. 22, 2021 to Final Office Action mailed Oct. 5, 2021", 9 pgs.

"U.S. Appl. No. 15/422,789, Response filed Dec. 18, 2019 to Non Final Office Action mailed Sep. 18, 2019", 11 pgs.

"U.S. Appl. No. 15/422,789, Response filed Jul. 9, 2019 to Restriction Requirement mailed May 9, 2019", 8 pgs.

"U.S. Appl. No. 15/422,789, Restriction Requirement mailed May 9, 2019", 6 pgs.

"U.S. Appl. No. 17/697,133, Non Final Office Action mailed Dec. 22, 2023", 6 pgs.

"U.S. Appl. No. 17/697,133, Notice of Allowance mailed May 31, 2024", 7 pgs.

"U.S. Appl. No. 17/697,133, Response filed Mar. 19, 2024 to Non Final Office Action mailed Nov. 22, 2023", 9 pgs.

"Chinese Application Serial No. 201780011122.2, Decision of Rejection mailed Sep. 9, 2021", with English translation, 16 pgs.

"Chinese Application Serial No. 201780011122.2, Office Action mailed Feb. 20, 2021", with English translation, 18 pgs.

"Chinese Application Serial No. 201780011122.2, Office Action mailed Jul. 3, 2020", w/ English translation, 23 pgs.

"Chinese Application Serial No. 201780011122.2, Response filed Apr. 13, 2022 to Examiner Telephone Consultation", w/ English Claims, 75 pgs.

"Chinese Application Serial No. 201780011122.2, Response filed May 7, 2021 to Office Action mailed Feb. 20, 2021", w/ English Claims, 12 pgs.

"Chinese Application Serial No. 201780011122.2, Response filed Nov. 9, 2020 to Office Action mailed Jul. 3, v20", w/ English claims, 22 pgs.

"Chinese Application Serial No. 201780011122.2, Response filed Dec. 23, 2021 to Decision of Rejection mailed Sep. 9, 2021", w/ English Claims, 17 pgs.

"European Application Serial No. 17706040.7, Communication Pursuant to Article 94(3) EPC mailed Oct. 12, 2021", 6 pgs.

"European Application Serial No. 17706040.7, Response filed Feb. 9, 22 to Communication Pursuant to Article 94(3) EPC mailed Oct. 12, 2021", 16 pgs.

"European Application Serial No. 17706040.7, Response filed Apr. 4, 19 to Communication Pursuant to Rules 161 and 162 mailed Sep. 28, 2018", 20 pgs.

"International Application Serial No. PCT/US2017/016150, International Preliminary Report on Patentability mailed Aug. 23, 2018", 8 pgs.

(56) References Cited

OTHER PUBLICATIONS

"International Application Serial No. PCT/US2017/016150, International Search Report mailed Apr. 7, 2017", 5 pgs.
"International Application Serial No. PCT/US2017/016150, Written Opinion mailed Apr. 7, 2017", 6 pgs.

* cited by examiner

SYSTEMS AND METHODS FOR PATIENT MONITORING

CLAIM OF PRIORITY

This application is a continuation of U.S. patent application Ser. No. 17/697,789, filed on Mar. 17, 2022, which is a continuation of U.S. patent application Ser. No. 15/422,789, filed on Feb. 2, 2017, which claims the benefit of priority under 35 U.S.C. § 119 (e) of U.S. Provisional Patent Application Ser. No. 62/294,555, filed on Feb. 12, 2016, which are herein incorporated by reference in their entireties.

TECHNICAL FIELD

This document relates generally to medical devices, and more particularly, to systems and methods for monitoring patients having medical device.

BACKGROUND

Congestive heart failure (CHF) is a leading cause of death in the United States. CHF occurs when the heart is unable to adequately supply enough blood to maintain a healthy physiological state. CHF may be treated by drug therapy, or by an implantable medical device (IMD) such as for providing cardiac electrostimulation therapies, including resynchronization therapy (CRT) to correct cardiac dyssynchrony within a ventricle or between ventricles.

CHF may have a huge economic impact on the healthcare system. Patients hospitalized with worsened heart failure such as decompensated heart failure may have a high rate of rehospitalization within six months. Rehospitalization is a principal factor responsible for the cost associated with heart failure management. Hospitals are typically concerned with reducing the number of unplanned readmissions as they may reflect upon the quality of treatment provided by the hospitals. An unplanned readmission occurs when a patient is readmitted to a hospital within a certain period of time (e.g., 30 days) after having been discharged from the hospital for treatment of the same or related condition, such as heart failure or pneumonia.

Premature hospital discharge is among the factors contributing to the high rate of rehospitalization, which may have been preventable if the patients receive proper care while admitted at the hospitals during the first visit or if the patients' length of stay had been extended. Proper patient monitoring, such as identification of proper treatment and effective assessment of patient responses to the treatment, is important for making reliable and robust patient disposition decisions such as discharge from or readmission to the hospital, which may reduce the rehospitalization rate and the associated cost.

SUMMARY

This document discusses, among other things, a patient management system for monitoring patients with a chronic disease, such as CHF. The patient management system may include a health status monitor that receives diagnostic data including physiological signals sensed from a patient using one or more implantable or other ambulatory sensors. The patient management system may operate on a selectable patient monitoring mode to assess patient readiness for discharge from a hospital or a risk of rehospitalization, at least based on the analysis of the sensor data. The assessment, such as a patient disposition decision, may be presented to a healthcare professional such as a clinician. The patient management system may include a therapy circuit to deliver a therapy to the patient based on the assessment.

In Example 1, a system for monitoring a patient is disclosed. The system may comprise a physiological sensor circuit that may include a sense amplifier circuit to sense one or more physiological signals and a filter circuit to generate one or more signal metrics from the sensed one or more physiological signals. The system may include health status analyzer circuit coupled to the physiological sensor circuit and configured to generate one or more stability indicators for the one or more signal metrics. The stability indicators may indicate stability of patient health status. The system may include an output unit to generate a human-perceptible presentation of the one or more stability indicators.

Example 2 may include, or may optionally be combined with the subject matter of Example 1 to optionally include, the health status analyzer circuit that may further be configured to generate one or more health status indicators for the one or more signal metrics. The health status indicators may indicate patient health status. The health status analyzer circuit may include a blending circuit to generate a patient disposition decision using the health status indicators and the stability indicators. The patient disposition decision may indicate readiness for patient discharge from or a risk of admission to a hospital.

Example 3 may include, or may optionally be combined with the subject matter of Example 2 to optionally include, a signal metric selector circuit that may select from the one or more signal metrics one or more mode-specific signal metrics according to a patient monitoring mode. The patient monitoring mode may include a pre-hospitalization mode, an in-hospital monitoring mode, or a post-discharge monitoring mode. The health status analyzer circuit may generate the patient disposition decision using health status indicators and stability indicators for the selected one or more mode-specific signal metrics.

Example 4 may include, or may optionally be combined with the subject matter of Example 3 to include, the health status analyzer circuit that may further include a physiological function analyzer circuit configured to produce one or more of a cardiac function indicator, a renal function indicator, or a pulmonary function indicator using respective one or more mode-specific signal metrics. The health status analyzer circuit may generate respective health status indicators and respective stability indicators using one or more of the cardiac function indicator, the renal function indicator, or the pulmonary function indicator.

Example 5 may include, or may optionally be combined with the subject matter of one or any combination of Examples 3 or 4 to include, the health status analyzer circuit that may generate the one or more health status indicators using a comparison between the selected one or more mode-specific signal metrics and respective reference levels, where the one or more health status indicators may indicate a progression of the patient health status.

Example 6 may include, or may optionally be combined with the subject matter of Example 5 to optionally include, the health status analyzer circuit that may generate the one or more health status indicators indicating a recovery of heart failure when a comparison between the selected one or more mode-specific signal metrics corresponding to the in-hospital monitoring mode and respective pre-hospitalization baseline levels satisfies a specified condition.

Example 7 may include, or may optionally be combined with the subject matter of Example 5 to include, the health status analyzer circuit that may generate the one or more health status indicators indicating worsening of heart failure when a comparison between the selected one or more mode-specific signal metrics corresponding to the post-discharge monitoring mode and respective pre-discharge baseline levels satisfies a specified condition.

Example 8 may include, or may optionally be combined with the subject matter of one or any combination of Examples 3 through 7 to include, the health status analyzer circuit that may generate the one or more stability indicators including variability of the selected one or more mode-specific signal metrics within a specified time period.

Example 9 may include, or may optionally be combined with the subject matter of one or any combination of Examples 3 through 8 to include, the sense amplifier circuit that may sense one or more physiological signals using a sampling rate based on the patient monitoring mode, or to digitize the one or more physiological signals using an analog-to-digital conversion resolution based on the patient monitoring mode, or the filter circuit that may generate the one or more signal metrics using one or more filter coefficients determined according to the patient monitoring mode.

Example 10 may include, or may optionally be combined with the subject matter of one or any combination of Examples 3 through 9 to include, the sense amplifier circuit that may further be configured to, in response to the in-hospital monitoring mode, sense the one or more physiological signals using a sampling rate determined according to a change or a rate of change of the one or more physiological signals within a specified time period prior to hospitalization.

Example 11 may include, or may optionally be combined with the subject matter of Example 10 to include, the sampling rate that is proportional to or inversely proportional to the change or the rate of change of the one or more physiological signals within a specified time period prior to hospitalization.

Example 12 may include, or may optionally be combined with the subject matter of one or any combination of Examples 2 through 11 to optionally include, the blending circuit that may generate, for the one or more signal metrics, a disposition score based on the health status indicators and the stability indicators.

Example 13 may include, or may optionally be combined with the subject matter of Example 12 to include, the blending circuit that may be configured to generate the patient disposition decision indicating readiness for patient discharge from a hospital if the disposition score corresponding to the in-hospital monitoring mode satisfies a discharge criterion, or to generate the patient disposition decision indicating a risk of patient readmission to a hospital if the disposition score corresponding to the post-discharge monitoring mode satisfies a readmission criterion.

Example 14 may include, or may optionally be combined with the subject matter of one or any combination of Examples 3 through 13 to include, a monitoring mode selector that may switch from the in-hospital monitoring mode to the post-discharge monitoring mode in response to the patient being discharge from a hospital, or switch from the post-discharge monitoring mode to the in-hospital monitoring mode in response to the patient being readmitted to a hospital.

Example 15 may include, or may optionally be combined with the subject matter of one or any combination of Examples 1 through 14 to include, a therapy circuit configured to deliver a therapy based at least on the one or more stability indicators.

In Example 16, a method for monitoring a patient using a monitor system is disclosed. The method may include steps of sensing one or more physiological signals using respective physiologic sensors, generating one or more signal metrics from the sensed one or more physiological signals, generating for the one or more signal metrics one or more stability indicators indicating stability of the patient health status, and producing a human-perceptible presentation of the one or more stability indicators.

Example 17 may include, or may optionally be combined with the subject matter of Example 16 to optionally include, steps of generating one or more health status indicators for the one or more signal metrics, the one or more health status indicators indicating patient health status, and generating a patient disposition decision using the health status indicators and the stability indicators, the patient disposition decision indicating readiness for patient discharge from or a risk of admission to a hospital.

Example 18 may include, or may optionally be combined with the subject matter of Example 17 to optionally include, selecting from the one or more signal metrics one or more mode-specific signal metrics according to a patient monitoring mode, where the patient monitoring mode may include a pre-hospitalization mode, an in-hospital monitoring mode, or a post-discharge monitoring mode. The patient disposition decision may be generated using health status indicators and stability indicators for the selected one or more mode-specific signal metrics.

Example 19 may include, or may optionally be combined with the subject matter of Example 17 to optionally include, the method of generating the one or more health status indicators that may include comparing the one or more signal metrics to respective reference levels, the health status indicators indicating a progression of the patient health status.

Example 20 may include, or may optionally be combined with the subject matter of Example 16 to optionally include, the method of generating the one or more stability indicators that may include determining variabilities of the one or more signal metrics within a specified time period.

Example 21 may include, or may optionally be combined with the subject matter of Example 18 to optionally include, the method of sensing the one or more physiological signals which may include one or more of sensing the one or more physiological signals using a sampling rate based on the patient monitoring mode, digitizing the one or more physiological signals using an analog-to-digital conversion resolution based on the patient monitoring mode, or filtering the one or more physiological signals using one or more filter coefficients based on the patient monitoring mode.

Example 22 may include, or may optionally be combined with the subject matter of Example 18 to optionally include, the method of sensing the one or more physiological signals that may include, in response to the in-hospital monitoring mode, sensing the one or more physiological signals using a sampling rate proportional to or inversely proportional to a change or a rate of change of the one or more physiological signals within a specified time prior to hospitalization.

Example 23 may include, or may optionally be combined with the subject matter of Example 18 to optionally include, the method of generating the patient disposition decision that may include generating a composite score using a weighting function of the health status indicators and the stability indicators, and generating the patient disposition decision indicating readiness for patient discharge from a hospital if the composite score corresponding to the in-hospital monitoring mode satisfies a discharge criterion, or a risk of patient readmission to a hospital if the composite score corresponding to the post-discharge monitoring mode satisfies a readmission criterion.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with a chronic disease such as a heart failure. The system may include a physiological sensor circuit to sense physiological signals and generate signal metrics from the physiological signals. The system may include a health status analyzer circuit to use the signal metrics to generate one or more stability indicators of patient health status, such as stability of heart failure status. The system may additionally generate one or more health status indicators indicating patient health status such as heart failure progression. A patient disposition decision may be generated using the health status indicators and the stability indicators to provide an indication of readiness for patient discharge from or a risk of admission to a hospital.

In this document, the terms "hospital", "hospitalization", "rehospitalization", "pre-hospitalization", or "post-hospitalization" are used. Although a traditional hospital is a non-limiting example of the patient care facility, these terms are to be contemplated to also refer to any other healthcare facilities or closely monitored environment, including urgent care centers, outpatient care centers, clinics, specialized care centers, ambulatory surgery centers, home care agencies, nursing homes, or assisted living houses, among other short-term or long-term care facilities. The systems, devices, and methods disclosed herein for patient monitoring may be used in any of these healthcare facilities.

Figure 1:
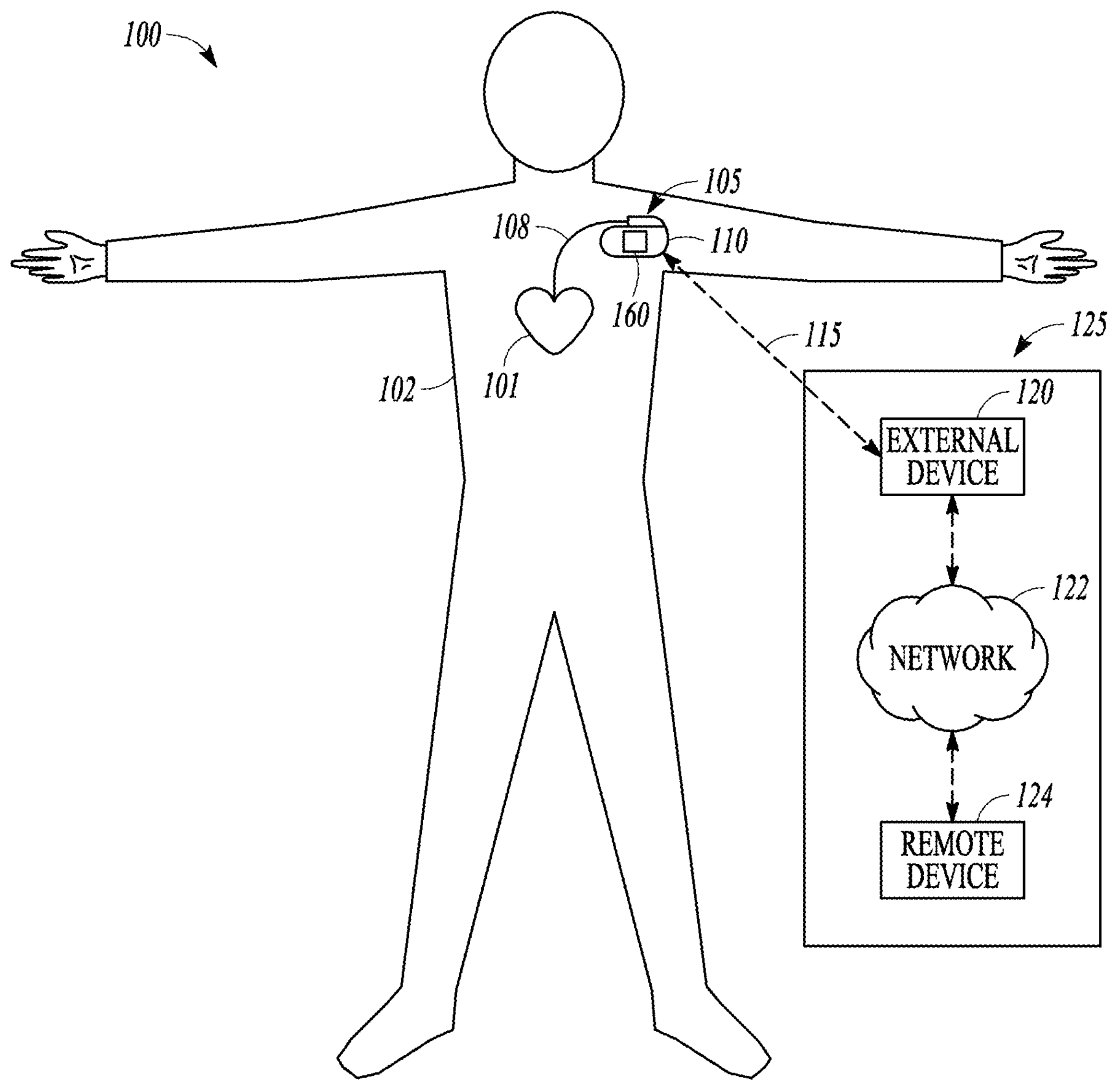
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices, or patient monitors, among others. The AMD 110 may alternatively or additionally include subcutaneously implanted devices such as a subcutaneous ICD or a subcutaneous diagnostic device, wearable medical devices such as patch based sensing device, or other external monitoring or therapeutic medical devices such as a bedside monitor.

The lead system 108 may include one or more transvenously, subcutaneously, or non-invasively placed leads or catheters. Each lead or catheter may include one or more electrodes for delivering pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. The arrangements and uses of the lead system 108 and the associated electrodes may be determined based on the patient need and the capability of the AMD 110.

The AMD 110 may house an electronic circuit for sensing a physiological signal, such as by using a physiologic sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature. The AMD 110 may initiate or adjust therapies based on the sensed physiological signals.

The patient management system 100 may include a health status monitor 160 providing for patient management using at least diagnostic data acquired by the ambulatory system 105. The health status monitor 160 may analyze the diagnostic data for patient monitoring, therapy assessment, risk stratification, patient discharge planning when the patient is hospitalized such as for worsened heart failure, or patient admission or readmission planning when the patient is not hospitalized or has been discharged from the hospital. In a non-limiting example as illustrated in FIG. 1, the health status monitor 160 may be substantially included in the AMD 110. Alternatively, the health status monitor 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of example and not limitation, and as illustrated in FIG. 1, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), delivering at least one therapy, or analyzing data associated with patient health conditions such as progression of heart failure.

Figure 2:
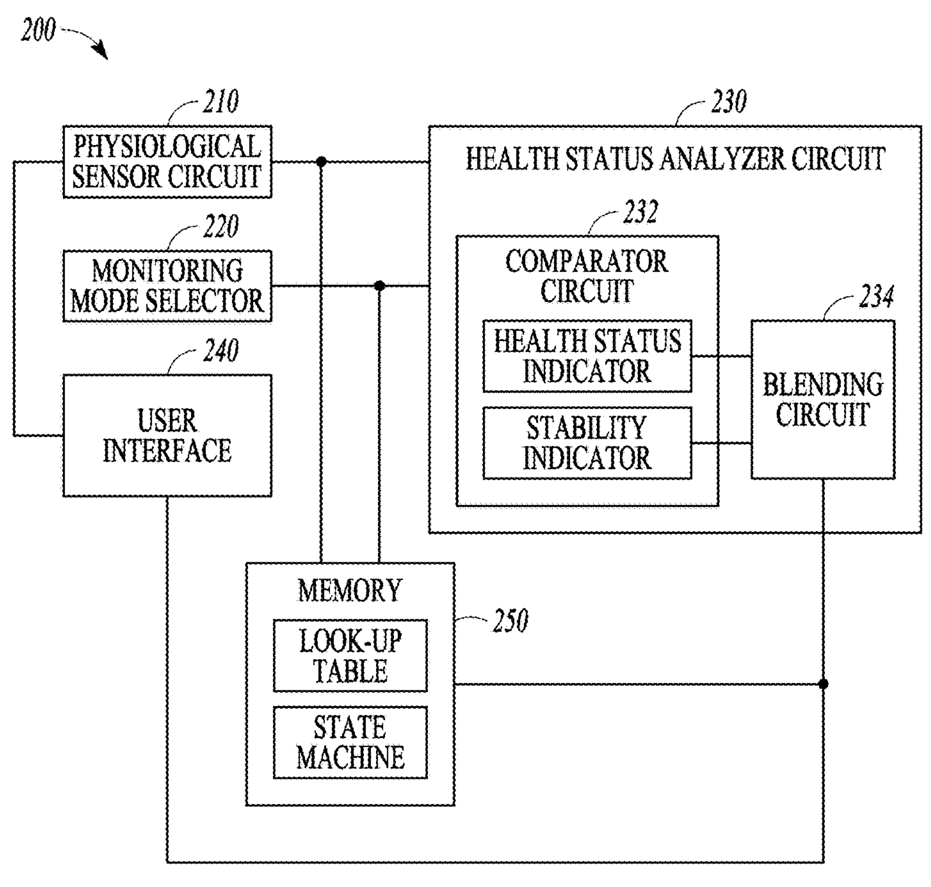
FIG. 2 illustrates generally an example of a patient monitoring system for assessing a patient's health status and the risk of hospitalization disposition.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals FIG. 2 illustrates generally an example of a patient monitoring system 200 for assessing a patient's health status and the risk of hospitalization disposition. The patient monitoring system 200 may include one or more of a physiological sensor circuit 210, a monitoring mode selector 220, a health status analyzer circuit 230, a user interface 240, and a memory 250. At least a portion of the patient monitoring system 200 may be implemented within the AMD 110, distributed between two or more implantable or wearable medical devices (such as an implantable medical device and a subcutaneous medical device), or distributed between the AMD 110 and the external system 125.

The physiologic sensor circuit 210 may include a sense amplifier circuit to sense one or more physiologic signals indicative of intrinsic physiologic activities, evoked physiologic activities when the heart is stimulated in accordance with a specified stimulation configuration, or physiologic activities under other specified conditions. The physiological sensor circuit 210 may be coupled to one or more electrodes such as on the lead system 108, or one or more implantable, wearable, or other ambulatory physiologic sensors, to sense the physiological signal(s). Examples of physiologic sensors may include pressure sensors, flow sensors, impedance sensors, accelerometers, microphone sensors, respiration sensors, temperature sensors, or blood chemical sensors, among others. Examples of the physiological signals sensed by the physiological sensor circuit 210 may include electrocardiograman electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, or a respiration signal, among others. The physiological sensor circuit 210 may additionally or alternatively be coupled to a storage device that stores the physiologic information, such as an external programmer, an electronic medical record (EMR) system, or a memory unit, among other data storage devices.

The sense amplifier circuit may process the one or more physiological signals, including, for example, amplification, digitization, filtering, or other signal conditioning operations. The physiological sensor circuit 210 may generate one or more signal metrics from the processed one or more physiological signals. The signal metrics may indicate patient's health status due to patient's disease progression, treatments, change in medication, or change in posture or activity levels, among others. In an example, the physiological sensor circuit 210 may receive a thoracic or cardiac impedance signal from the electrodes on the lead system 108, and generate a signal metric of impedance magnitude within a specified frequency range. In another example, the physiological sensor circuit 210 may sense a HS signal from an accelerometer, a microphone, or an acoustic sensor coupled to the AMD 110, and generate two or more HS metrics. Examples of the HS metrics may include intensities of S1, S2, S3, or S4 heart sounds, or timing of the S1, S2, S3, or S4 heart sound with respect to a fiducial point such as a P wave, Q wave, or R wave in an ECG. In an example, the physiological sensor circuit 210 may receive multiple physiological signals from multiple sensors. For example, the physiological sensor circuit 210 may receive a blood pressure signal from a pressure sensor and generate two or more blood pressure signal metrics which may include systolic blood pressure, diastolic blood pressure, mean arterial pressure, and the timing metrics of these pressure measurements with respect to a fiducial point.

The monitoring mode selector 220 may receive a selection between two or more patient monitoring modes, including a pre-hospitalization mode before the patient is admitted to a hospital, an in-hospital monitoring mode when the patient is being hospitalized, or a post-discharge monitoring mode when the patient has been discharged from the hospital. The monitoring mode selector 220 may be coupled to the user interface 240, which may include a user input device that enables a user to input a selection of a monitoring mode, or an indication of patient hospitalization status (e.g., patient being hospitalized or discharged from the hospital).

The physiological sensor circuit 210 and the monitoring mode selector 220 may be coupled to the memory 250. The signal metrics generated from the physiological signals and the selection of the monitoring mode may be saved in the memory 250. As illustrated in FIG. 2, the memory 250 may store a pre-determined look-up table or an association map establishing a correspondence between the monitoring modes and the corresponding signal metrics (which are referred to hereinafter as "mode-specific signal metrics") for use in analyzing patient health status. The look-up table or an association map may additionally establish a correspondence between the monitoring modes and the parameters used for processing the physiological signals, or algorithms used for assessing patient health status using the mode-specific signal metrics (which are collectively referred to hereinafter as "mode-specific health status analysis"). In an example, parameters used for processing the physiological signals, such as sampling frequency, analog-to-digital conversion resolution, or filter coefficients may be determined based on the selected monitoring mode. In an example, weighting functions may be generated and applied to respective signals metrics to produce a composite indicator indicating the patient's discharging readiness or readmission risk, where the weight functions may be determined based on the selected monitoring mode. In another example, one or more threshold or range values used for detecting the degree of change of the signal metrics may be determined based on the selected monitoring mode. In yet another example, one or more parameters controlling therapy delivery, and the therapy types, may be selected based on the monitoring mode. Examples of the mode-specific health status analysis are discussed below, such as with reference to FIGS. 4-5.

The memory 250 may also store a state machine that comprises various patient monitoring modes and transitions between the monitoring modes when specified triggering events occur or conditions are satisfied. In an example, the monitoring mode selector 220 may automatically switch the patient monitoring from a first monitoring mode to a different second monitoring mode according to the state machine stored in the memory 250 and upon a detection of a mode-switch triggering event, such as a patient disposition decision generated by the health status analyzer circuit 230. Examples of the state machine and transitions between monitoring modes are discussed below, such as with reference to FIG. 3.

In some examples, the health status analyzer circuit 230 may be implemented as a part of a microprocessor circuit. The microprocessor circuit may be a dedicated processor such as a digital signal processor, application specific integrated circuit (ASIC), microprocessor, or other type of processor for processing information including the physiologic signals received from the physiological sensor circuit 210. Alternatively, the microprocessor circuit may be a general purpose processor that may receive and execute a set of instructions of performing the functions, methods, or techniques described herein.

In some examples, the health status analyzer circuit 230 may include sets comprising one or more other circuits or sub-circuits, such as a comparator circuit 232 and a blending circuit 234 circuit. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The comparator circuit 232, coupled to the physiological sensor circuit 210 and the monitoring mode selector 220, may generate from the one or more signal metrics (such as the mode-specific signal metrics stored in the memory 250) respective health status indicators indicating patient health status, and respective stability indicators indicating stability of the patient health status. In some examples, the comparator circuit 232 may include separate circuits that respectively generate the health status indicators and the stability indicators. The comparator circuit 232 may generate the health status indicators using a comparison between a mode-specific signal metric (X) and a respective reference level ($X_{Ref}$). The relative difference $\Delta X$ may indicate a progression of patient health status, such as worsening of heart failure when the patient is not hospitalized (pre-hospitalization or discharged from a hospital), or recovery of heart failure when the patient is being hospitalized. In an example, the comparator circuit 232 may compute a relative difference ($\Delta X$) between X and $X_{Ref}$, such as a deviation $\Delta X = X - X_{Ref}$, or alternatively as percentage change $\Delta X = (X - X_{Ref})/X_{Ref}$. The relative difference $\Delta X$ may be compared to a threshold or a specified range to provide the health status indicator. The health status indicator may be represented by a categorical value, or a numerical value based on a comparison of the relative difference $\Delta X$ to multiple threshold values.

The reference level $X_{Ref}$ may be determined using multiple historical measurements of the signal metric X under a monitoring mode which may be different than the present monitoring mode. In an example, the reference $X_{Ref}$ may be a pre-hospitalization baseline determined as a mean, median, or other central tendency index of multiple measurements of the signal metric X during a pre-hospitalization period when the patient is free of heart failure decompensation or other target events. In another example, the reference $X_{Ref}$ may be an in-hospital baseline level of the signal metric X over a specified in-hospital period when the patient is deemed to be recovered from the target disease and remains stable over a specified period of time. The reference level $X_{Ref}$ may be stored in the memory 250.

In computing the relative difference ($\Delta X$) under a first monitoring mode, the comparator circuit 232 may use one or more signal metrics obtained during the first monitoring mode and a respective reference level ($X_{Ref}$) corresponding to a second different monitoring mode. For example, when a patient is being hospitalized for worsening heart failure and monitored under the in-hospital monitoring mode, the comparator circuit 232 may generate the health status indicators indicating a recovery of heart failure using a comparison between the mode-specific signal metrics obtained during the in-hospital monitoring mode and the respective pre-hospitalization baseline levels $X_{Ref}$. In another example, after the patient has been discharged from the hospital and being monitored under the post-discharge monitoring mode, the comparator circuit 232 may generate the health status indicators indicating worsening of heart failure using a comparison between the mode-specific signal metrics obtained during the post-discharge monitoring mode and in-hospital baseline levels $X_{Ref}$.

In addition to or in lieu of the relative difference between the mode-specific signal metric (X) and a respective reference level ($X_{Ref}$), the comparator circuit 232 may generate the health status indicators based on a comparison between a change or a rate of change of a signal metric during a first monitoring mode, and a change or a rate of change of the signal metric during a different second monitoring mode. For example, when a patient is being hospitalized for worsening heart failure, the comparator circuit 232 may determine a change or rate of change of a mode-specific signal metric (X) during an in-hospital period of time, compare such change or rate of change to a corresponding change or rate of change of the same signal metric during a pre-hospitalization period of time leading up to the hospitalization, and generate the health status indicators when the change or rate of change of the signal metric during the in-hospital monitoring mode falls within a specified margin of the change or rate of change of X during the pre-hospitalization monitoring mode.

The comparator circuit 232 may generate the stability indicators using variability of one or more mode-specific signal metrics within a specified time period during a patient monitoring mode, such as approximately 1-14 hours or 1-7 days. Examples of the variability may include a range, a quartile range, a percentile range, a standard deviation, a variance, a coefficient of variance, a skewness or histogram, or a measure of dispersion, among others. The stability indicator may be represented by a categorical value, or a numerical value such as a stability score, such as based on a comparison of the variability of the one or more mode-specific signal metrics to various threshold values. In an example, the filter circuit may include a filter coefficient selected to attenuate circadian variation of the sensed one or more physiological signals. The variability of the signal metrics generated from the filtered physiological signals may thus be less affected by the circadian variation of the physiological signal. The resulting stability indicators of the mode-specific signal metrics may be more reliably reflect the stability of patient health status.

The blending circuit 234 may be coupled to the comparator circuit 232, and may generate a patient disposition decision using the health status indicators and the stability indicators. The patient disposition decision may indicate a risk of patient admission or readmission to, or readiness for discharge from, a hospital. The stability indicator associated with a signal metric X may be correlative of stability of the patient health condition. Such information of patient stability may not otherwise be presented in the health status indicator (such as the relative difference $\Delta X$). The use of the stability indicator may reduce the likelihood of improper patient disposition, such as premature patient discharge or unnecessary rehospitalization in certain patients. Therefore, a patient monitoring system that utilizes both the health status indicator and the stability indicator may provide more accurate assessment of patient health status such as progression of a chronic disease, and therefore a more reliable disposition decision.

The patient disposition decision may be based on the health status indicator and the stability indicator each satisfying respective conditions, such as when the relative difference $\Delta X$ between the signal metric X and the corresponding reference level $X_{Ref}$ falls below a specified progression threshold, and the variability of the signal metric X falls below a specified variability threshold. In an example, when a patient is hospitalized for worsened heart failure, a signal metric of S3 heart sound intensity $\|S3\|$, among other signal metrics, may be used for in-hospital monitoring to assess patient recovery. A $\|S3\|$-based disposition score, $DS_{\|S3\|}$, may be generated based on (1) a relative difference between the in-hospital $\|S3\|$ and a pre-hospitalization baseline $\|S3\|_{Ref}$, and (2) the stability of the in-hospital $\|S3\|$ during the in-hospital mode, such as a variability of $\|S3\|$ (var($\|S3\|$)) across multiple in-hospital $\|S3\|$ measurements. If $\|S3\|$ decreases to a specified margin of the pre-hospitalization baseline level $\|S3\|_{Ref}$, and the var($\|S3\|$) falls below a threshold value, then $DS_{\|S3\|}$ has a score of "1", indicating patient's readiness to be discharged from the hospital, based on the signal metric $\|S3\|$. If either the health status indicator or the stability indicator fails to satisfy the respective condition, then the $DS_{\|S3\|}$ has a score of "0", indicating patient's not being ready for discharge. That is, $$DS_{\|S3\|} = \begin{cases} 1, \text{ if } \dfrac{\|S3\| - \|S3\|_{Ref}}{\|S3\|_{Ref}} < T_1, \text{ AND var}(\|S3\|) < T_2 \\ 0, \text{ otherwise} \end{cases} \quad (1)$$

where $T_1$ and $T_2$ denote respective threshold values for the relative difference of $\|S3\|$ and the variability of $\|S3\|$. In an example, the threshold $T_1$ may be approximately 10%. In an example, the threshold $T_2$ may be approximately 10%. In another example, the threshold $T_2$ may be approximately 40%.

In some examples, the blending circuit 234 may generate a patient disposition decision using a combination of the health status indicators and the stability indicators corresponding to some of all of the one or more signal metrics, such as {X(i)}={X(1), X(2), . . . , X(N)} where N denotes the number of signal metrics. The blending circuit 234 may generate for each signal metric X(i) a respective disposition score DS(i) based on the corresponding health status indicator (such as the relative difference $\Delta X(i)$) and the corresponding stability indicator (such as the variability measure var(X(i))). The disposition score DS(i) may indicate a risk associated with patient disposition (such as patient hospitalization, discharge, or readmission) based on the evidence of the signal metric X(i). The combination of {DS(i)} (corresponding to the signal metrics {X(i)}) may include a linear or a nonlinear combination. In an example, the blending circuit 234 may generate a composite disposition score cDS using a linear weighted combination of the {DS(i)}:

$$cDS = \sum_{i=1}^{N} w_i \cdot DS(i) \quad (2)$$

where $w_i$ denotes the weight factor for DS(i). The weight functions $w_i$ may be determined based on signal use or signal characteristics of the corresponding signal metric X(i) during a particular patient monitoring mode. In an example, prior to patient hospitalization, if a signal metric X(i) is used but another signal metric X(j) is not used for detecting worsening HF which leads to patient hospitalization, then during the in-hospital mode a larger weight $w_i$ may be applied to DS(i) while a smaller weight $w_j$ ($w_j<w_i$) may be applied to DS(j). In another example, prior to patient hospitalization, if a signal metric X(i) demonstrates more profound change than another signal metric X(j) during a time period leading to an event of HF decompensation and patient hospitalization, then during the in-hospital mode the weight $w_i$ applied to DS(i) may be greater than the weight $w_j$ applied to DS(j). In an example, a plurality of signal metrics including ||S3||, thoracic impedance (Z), rapid shallow breathing index (RSBI), and heart rate (HR) are used in in-hospital monitoring to assess patient recovery from a heart failure event leading to the hospitalization. The blending circuit 234 may generate the cDS as: $cDS=w_1 \cdot DS_{||S3||}+w_2 \cdot DS_Z+w_3 \cdot DS_{RSBI}+w_4 \cdot DS_{HR}$, where $w_1$ through $w_4$ denote weight factors for the respective progression score. If ||S3|| and Z are used and RSBI and HR are not used for pre-hospitalization detection of worsening HF, or if ||S3|| and Z each demonstrates more significant change leading to hospitalization than RSBI and HR, then $w_1$ and $w_2$ may be larger than $w_3$ and $w_4$. In an example, $w_1=w_2=1$, and $w_3=w_4=0.5$. The blending circuit 234 may alternatively compute a nonlinear combination of the disposition scores, such as by using a decision tree, a neural network, a fuzzy-logic model, or a multivariate regression model, among others.

While an individual DS(i) indicates a risk associated with patient disposition based on the evidence provided by the signal metric X(i), the composite disposition score cDS may provide a comprehensive assessment of the risk associated with patient disposition. For example, a larger cDS may indicate a lower risk associated with switching the patient to a different hospitalization status or monitoring mode, such as discharging the patient, or readmitting the patient. In an example, the blending circuit 234 may generate a patient disposition decision if the cDS exceeds a threshold value or falling within a specified range. An exemplary threshold value may be approximately 1.5. In an example, the blending circuit 234 may generate the patient disposition decision indicating readiness for patient discharge from a hospital if the composite disposition score corresponding to the in-hospital monitoring mode satisfies a discharge criterion. In another example, the blending circuit 234 may generate the patient disposition decision indicating a risk of patient readmission to a hospital if the composite disposition score corresponding to the post-discharge monitoring mode satisfies a readmission criterion. The blending circuit 234 may be coupled to the memory 250 to store in the memory 250 information including the disposition scores (DS(i)) of the signal metrics, the composite disposition score cDS, and the patient disposition decision.

The user interface 240 may include a user input device and an output unit such as a display. In an example, at least a portion of the user interface 240, such as the output unit, may be implemented in the external system 125. Examples of the input device may include a keyboard, on-screen keyboard, mouse, trackball, touchpad, touch-screen, or other pointing or navigating devices. The user input device may be coupled to the physiological sensor circuit 210 to enable a system user to program one or more parameters used for sensing the physiologic signals. The user input device may also be coupled to the monitoring mode selector 220, which may receive a user command such as a selection of the monitoring mode among a pre-hospitalization mode, an in-hospital monitoring mode, and a post-discharge monitoring mode. In an example, the monitoring mode selector 220 may automatically determine whether or not to switch to a different patient monitoring mode based on the state machine, the existing patient monitoring mode, and an event that may trigger a transition to the different patient monitoring mode such as a patient disposition decision generated by the blending circuit 234. The user command may include confirmation or modification of the automatic selection of the monitoring mode, such as based on the patient being discharged from or admitted to a hospital.

The output unit may generate a human-perceptible presentation of the patient disposition decision and displayed on the display. The output unit may also display information including the physiological signals sensed by the physiological sensor circuit and the signals metrics generated from the physiological signals, heath status indicators and stability indicators associated with the signal metrics, device status such as lead impedance and integrity, battery status such as remaining lifetime of the battery, or cardiac capture threshold, among others. The output unit may also display a plurality of selectable patient monitoring modes and the current selection of the patient monitoring mode. The information may be presented in a table, a chart, a diagram, or any other types of textual, tabular, or graphical presentation formats, for displaying to a system user. The presentation of the output information may include audio or other human-perceptible media format to alert the system user of a transition from one patient monitoring mode to another different patient monitoring mode.

In some examples, the patient monitoring system 200 may additionally include a therapy circuit configured to deliver a therapy to the patient such as in response to one or more of the stability indicator, the health status indicator, or the patient disposition decision. Examples of the therapy may include electrostimulation therapy delivered to the heart, a nerve tissue, or other target tissues in response to the detection of the target physiological event, or drug therapy including delivering drug to a tissue or organ. In some examples, the stability indicator, the health status indicator, or the patient disposition decision may be used to modify an existing therapy, such as adjusting a stimulation parameter or drug dosage.

Figure 3:
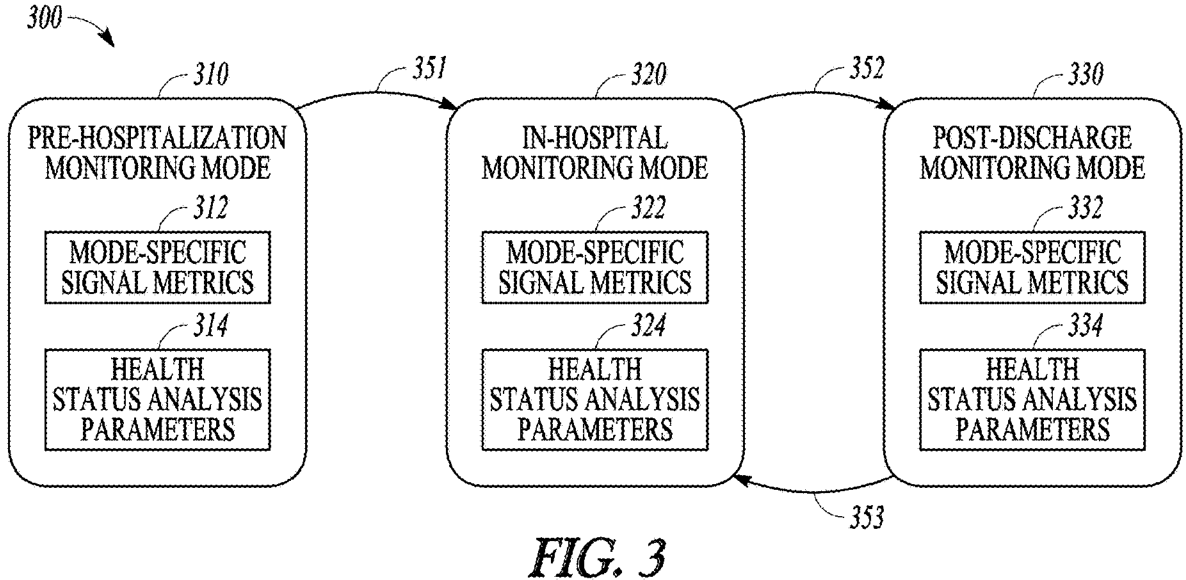
FIG. 3 illustrates generally a diagram of state transitions between patient monitoring modes.

FIG. 3 illustrates generally a diagram 300 of state transitions between two or more patient monitoring modes, which may be an embodiment of the state machine as stored in the memory 250. By way of example and no limitation, and as illustrated in FIG. 3, the state machine may comprise a pre-hospitalization monitoring mode ($M_{PreH}$) 310, an in-hospital monitoring mode ($M_H$) 320, and a post-discharge monitoring mode ($M_{PostH}$) 330. Associated with each monitoring mode include one or more mode-specific signal metrics (such as one of 312, 322, or 332) and one or more health status analysis parameters (such as one of 314, 324, or 334). The mode-specific signal metrics and the health status analysis parameters may be stored in the memory 250, and may be used by the health status analysis circuit 230 for determining patient health status including the health status indicators and the stability indicators, and for generating the patient disposition decision.

The signal metrics associated with one monitoring mode may be different from the signal metrics associated with another monitoring mode. In an example, at least one signal metric associated with one monitoring mode is not associated with another monitoring mode. In an example, at least one signal metric may be shared by two different patient monitoring modes. In some examples, a signal metrics associated with a first monitoring mode and another signal metric associated with a second monitoring mode, although not identical from each other, may be generated from the a physiological signal sensed from the same physiological sensor. For example, a signal metric of S1 heart sound intensity (||S1||) generated from a heart sound signal sensed from a heart sound sensor may be used for in-hospital monitoring mode $M_H$ but not in the pre-hospitalization mode $M_{PreH}$, and a S3 heart sound intensity (||S3||) generated from the heart sound signal using the same heart sound sensor may be included in the pre-hospitalization mode $M_{PreH}$ but not in the in-hospital monitoring mode $M_H$.

The mode-specific signal metrics for the respective patient monitoring mode may be chosen based on information about the ambient environment in which a physiological sensor is used, patient physical or health condition, responsiveness of a physiologic sensor to a particular type of therapy, or sensitivity of a signal metric to progression of patient health status, among others. For example, based on the information that patient is physically less active during hospitalization than during pre- or pose-hospitalization, signal metrics characterizing physical activity (such as activity intensity, frequency, or duration) or utilizing information about physical activity (such as physiologic response to activity, PRA, or signal metrics based on a correlation between the physical activity and other physiological parameter) may be excluded from the mode-specified signal metrics 322 associated with the in-hospital monitoring mode $M_H$; however, such physical activity-related signal metrics may be included in the signal metrics 312 or 332 respectively associated with the pre-hospitalization or post-discharge monitoring modes. In another example, while ||S3|| may be useful in detecting events such as HF decompensation that may lead to hospitalization, it may be less sensitive to acute hemodynamic changes in some patients, or less responsive to acute therapies at hospital, than other signal metrics such as thoracic impedance (Z) or S1 heart sound intensity ||S1||. As such, while ||S3|| may be included in the signal metrics 312 during pre-hospitalization monitoring, ||S1|| or Z may be more suitable than ||S3|| during in-hospital monitoring and thus may be included in the signal metrics 322. The mode-specific signal metrics may additionally or alternatively be chosen based on a target disease or condition to monitor, such as heart failure, pulmonary edema, chronic obstructive pulmonary disease (COPD), pneumonia, myocardial infarction, dilated cardiomyopathy (DCM), ischemic cardiomyopathy, valvular disease, renal disease, peripheral vascular disease, cerebrovascular disease, hepatic disease, diabetes, anemia, depression, pulmonary hypertension, sleep disordered breathing, hyperlipidemia, among others.

The health status analysis parameters 314, 324 and 334 may include parameters used for processing the physiological signals or generating the signal metrics, such as sampling frequency, analog-to-digital conversion resolution, or filter coefficients, among others. The health status analysis parameters may additionally include one or more thresholds for detecting the degree of change of the signal metrics, or weighting functions applied to the patient disposition scores, or linear or nonlinear combination algorithms as used by the blending circuit 234 for generating the composite disposition score and the disposition decision.

Transition from a first monitoring mode to a different second monitoring mode may be triggered by a mode-switch triggering event, such as a patient disposition decision generated by the blending circuit 234. As previously discussed, when the composite disposition score cDS satisfies a specified condition (such as cDS exceeding a threshold value), a patient disposition decision such as hospitalization readiness, discharge readiness, or re-admission readiness may be generated. As illustrated in FIG. 3, a transition 351 from the pre-hospitalization monitoring mode to the in-hospital monitoring mode may be established in response to a hospitalization readiness decision produced at the blending circuit 234. A transition 352 from the in-hospital monitoring mode to the post-discharge monitoring mode may be established in response to a discharge readiness decision. A transition 353 from the post-discharge monitoring mode to the in-hospital monitoring mode may be established in response to a readmission readiness decision. The monitoring mode selector 220 may automatically, or additionally at least in part based on a user input, perform patient monitoring mode switch according to the state machine diagram 300.

Figure 4:
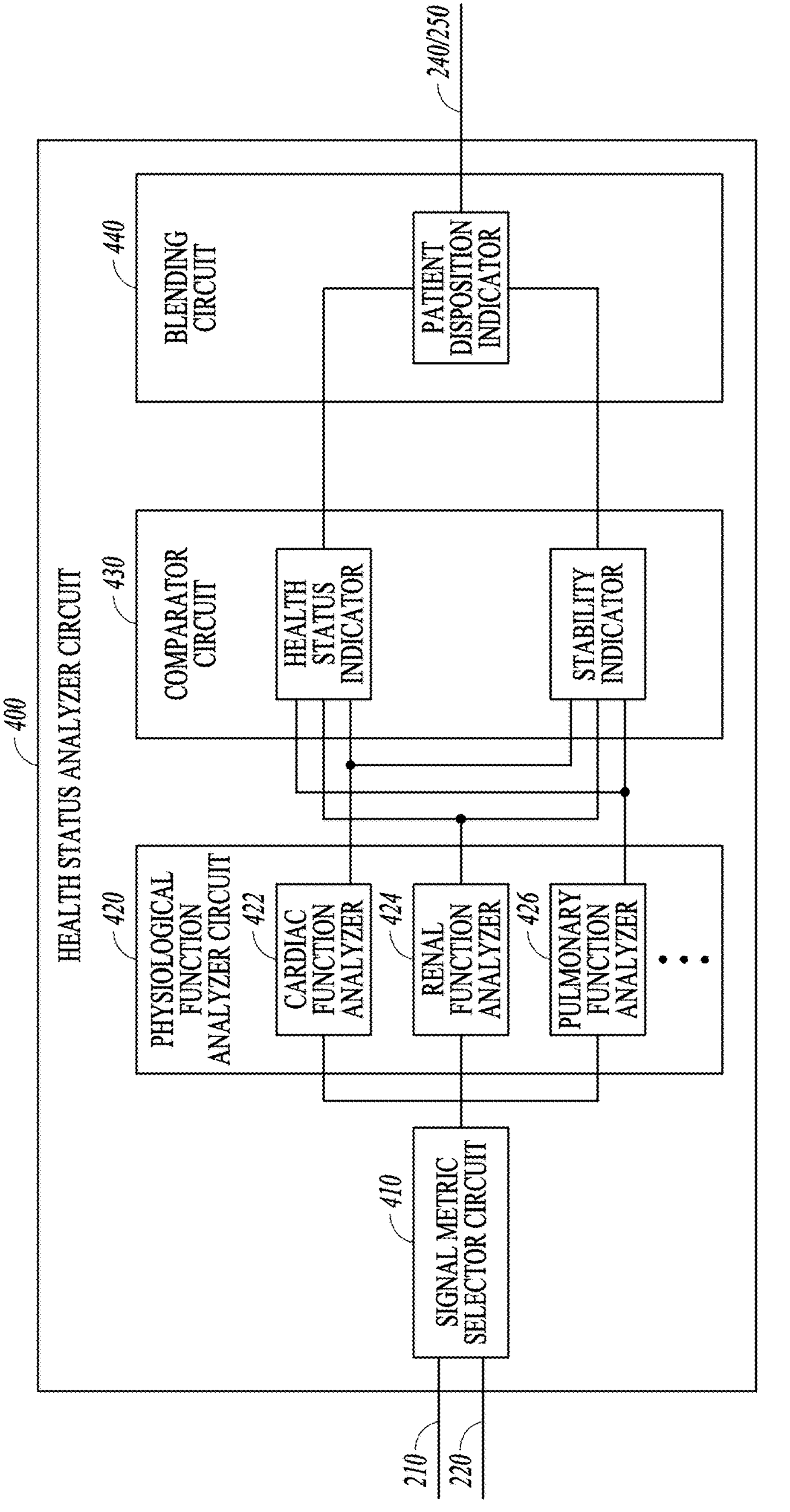
FIG. 4 illustrates generally an example of a health status analyzer circuit for generating a patient disposition decision.

FIG. 4 illustrates generally an example of a health status analyzer circuit 400 for generating a patient disposition decision, which may be an embodiment of the health status analyzer circuit 230 as illustrated in FIG. 2. The health status analyzer circuit 400 may include a comparator circuit 430 and a blending circuit 440, which may be respective embodiment of the comparator circuit 232 and the blending circuit 234 of the health status analyzer circuit 230. The health status analyzer circuit 400 may additionally include a signal metric selector circuit 410 or a physiological function analyzer circuit 420. In some examples, the health status analyzer circuit 400 may be implemented as a part of a microprocessor circuit, such as a digital signal processor, application specific integrated circuit (ASIC), microprocessor, or a general purpose processor that may receive and execute a set of instructions of performing the functions, methods, or techniques described herein.

The signal metric selector circuit 410 may select from the one or more signal metrics one or more mode-specific signal metrics according to the selected monitoring mode. The mode-specific signal metrics may be selected in accordance with the look-up table or an association map stored in the memory 250, which establishes a correspondence between the monitoring modes and the corresponding signal metrics or parameters for use signal processing or patient health status analysis. The signal metric selector circuit 410 may additionally select, for one or more physiological function analyzers in the physiological function analyzer circuit 420, a respective set of signal metrics suitable for analyzing respective physiological functions. By way of example of not limitation, and as illustrated in FIG. 4, the physiological function analyzer circuit 420 may include one or more of a cardiac function analyzer 422, a renal function analyzer 424, or a pulmonary function analyzer 426, among others. The signal metrics selected for one physiological function analyzer may be different from the signal metrics selected for another physiological function analyzer such as by at least one signal metric. In an example, a signal metric may be selected for two or more physiological function analyzers. Examples of signal metrics ($\{X_C(i)\}=\{X_C(1), X_C(2), \ldots, X_C(N)\}$) for cardiac function analyzer 422 may include heart rate, heart rate variability, morphological feature extracted from a ECG or an electrogram, intrathoracic impedance, pulmonary arterial pressure, activity level, posture, S1 heart sound strength, S3 heart sound strength, systolic timing interval, or pre-ejection and ejection time, ventricular pressure, or pulmonary arterial pressure, among others. Examples of signal metrics ($\{X_R(j)\}=\{X_R(1), X_R(2), \ldots, X_R(M)\}$) for renal function analyzer 424 may include creatinine level, body urea nitrogen (BUN) level, BUN/creatinine ratio, or glomerular filtration rate (GFR), among others. Examples of signal metrics ($\{X_P(k)\}=\{X_P(1), X_P(2), \ldots, X_P(K)\}$) for pulmonary function analyzer 426 may include respiration rate, rapid shallow breathing index, tidal volume, thoracic impedance, heart sounds, heart rates, or pulmonary arterial pressure, among others.

Each physiological function analyzer circuit may use the respective mode-specific signal metrics to generate respective indications of a particular physiological functionality during a specified patient monitoring mode. For example, the cardiac function analyzer 422 may produce cardiac function indicators which may include cardiac function progression such as the relative difference $\Delta X_C(i)$ of a signal metric $X_C(i)$ from a reference level $X_{C\text{-}Ref}(i)$), and cardiac stability indicators such as a variability measure of $X_C(i)$ over a specified period of time during a particular patient monitoring mode. Similarly, the renal function analyzer 424 may produce renal function indicators which may include renal function progression indicators such as the relative difference $\Delta X_R(j)$ of a signal metric $X_R(j)$ from a reference level $X_{R\text{-}Ref}(j)$), and renal stability indicators such as a variability measure of $X_R(j)$. Likewise, the pulmonary function analyzer 426 may produce pulmonary function indicators which may include pulmonary function progression indicators such as the relative difference $\Delta X_P(k)$ of a signal metric $X_P(k)$ from a reference level $X_{P\text{-}Ref}(k)$), and pulmonary stability indicators such as a variability measure of $X_P(k)$. The reference levels $X_{C\text{-}Ref}(i)$, $X_{R\text{-}Ref}(j)$, and $X_{P\text{-}Ref}(k)$ may each be determined using multiple historical measurements obtained during a monitoring mode, which may be different than the present monitoring mode.

The comparator circuit 430, coupled to the various physiological function analyzer circuits 422, 424, and 425, may generate one or more health status indicators and one or more stability indicators using one or more of the cardiac function indicators, the renal function indicators, or the pulmonary function indicators. In an example, the health status indicator may be an aggregation, or a linear or nonlinear combination of one or more of the cardiac function progression indicator, the renal function progression indicator, and the pulmonary function progression indicator. In an example, the stability indicator may be an aggregation, or a linear or nonlinear combination of one or more of the cardiac function stability indicator, the renal function stability indicator, and the pulmonary function stability indicator. Monitoring and analyzing multiple physiological functions, such as cardiac, pulmonary, or renal functions, may provide a comprehensive assessment of patient health status such as progression of a chronic disease. A disposition decision based on multiple physiological functions may reduce the likelihood of improper patient disposition such premature discharge or unnecessary rehospitalization. The multiple physiological functions may also be used to determine the effectiveness of a treatment plan or a particular therapy, or to guide a titration of therapy type or dosage. The progression indicators and the stability indicators associated with one or more of the physiological function analyzers 422, 424 and 426, and the combine health status indicator or the combined stability indicator as provided by the comparator circuit 430, may be stored in the memory 250, and/or presented in a display of the user interface 240.

The blending circuit 440 may generate a patient disposition decision using the health status indicators and the stability indicators such as provided by the comparator circuit 430. Similar to the blending circuit 234 as illustrated in FIG. 2, the blending circuit 440 may generate, for one or more of the cardiac signal metrics $\{X_C(i)\}$, the renal signal metrics $\{X_R(j)\}$, or the pulmonary signal metrics $\{X_P(k)\}$, respective disposition scores $DS_C(i)$, $DS_R(j)$, or $DS_P(k)$. The disposition score may be based on the relative difference (e.g., $\Delta X_C(i)$, $\Delta X_R(j)$, or $\Delta X_P(k)$) and the variability measure (e.g., $var(X_C(i))$, $var(X_R(j))$, or $var(X_P(k))$) each satisfying a specified condition. In an example, the blending circuit 440 may generate a plurality of physiological function-indicated composite disposition scores, such as a cardiac function-indicated composite disposition score $cDS_C$, a renal function-indicated composite disposition score $cDS_R$, or a renal function-indicated composite disposition score $cDS_R$. The $cDS_C$ may be computed using a combination of the disposition scores corresponding to some or all of N cardiac signal metrics $\{X_C(i)\}$. Similarly, the $cDS_R$ may be computed using a combination of the disposition scores corresponding to some or all of M renal signal metrics $\{X_R(j)\}$, and the $cDS_P$ may be computed using a combination of the disposition scores corresponding to some or all of K pulmonary signal metrics $\{X_P(k)\}$. In an example, the combination may be a linear weighted combination, such as show in Equation (3) as follows:

$$\begin{cases} cDS_C = \sum_{i=1}^{N} w_i \cdot DS_C(i) \\ cDS_R = \sum_{j=1}^{M} w_j \cdot DS_R(j) \\ cDS_P = \sum_{k=1}^{K} w_k \cdot DS_P(k) \end{cases} \quad (3)$$

Similar to the discussion with reference to the blending circuit 234 in FIG. 2, the weight functions $w_i$, $w_j$, and $w_k$ may each be determined based on signal use or signal characteristics of the corresponding signal metric during a particular patient monitoring mode.

The physiological function-indicated composite disposition scores, such as the $cDS_C$, the $cDS_R$, and the $cDS_P$, may be presented on the display of the user interface 240, and stored in the memory 250. As an intermediate level of risk assessment between a signal metric-based risk DS(i) and the comprehensive cDS, the physiological function-indicated composite disposition scores may each indicate a risk associated with a patient disposition decision based on a particular physiological function of the patient (e.g., cardiac, renal, or pulmonary function). The physiological function-indicated composite disposition scores may additionally be used for diagnosing commodities, or titrating therapies when the patient is monitored according to a particular monitoring mode. Some or all of the physiological function-indicated composite disposition scores may be combined to produce the patient disposition decision. In an example, a patient disposition such as readiness for patient discharge or a risk of rehospitalization may be generated if the $cDS_C$, the $cDS_R$, and the $cDS_P$ each exceeds respectively specified threshold or falls within a respectively specified range. In an example, the blending circuit 440 may compute a combination of the $cDS_C$, the $cDS_R$, and the $cDS_P$, such as a linear weighted combination:

$$cDS = a_1 \cdot cDS_C + a_2 \cdot cDS_R + a_3 \cdot DS_P \tag{4}$$

where the weight factors $a_1$ through $a_3$ may each be specified or adjusted by the user based on the patient health condition or target disease. For example, if a patient is hospitalized for pulmonary edema, then a larger weight $a_3$ may be applied to the pulmonary function-indicated disposition score DS is hospitalized for worsening pulmonary edema, then a larger weight $a_3$ may be applied to the pulmonary function-indicated disposition score $DS_P$ because an indication of pulmonary function recovery may play a decisive role in assessing the patient's readiness to be discharged from the hospital. In another example, if a patient is hospitalized for HF decompensation, then the weights $a_1$, $a_2$ and $a_3$ may be substantially equally weighted, because recovery of cardiac, renal, and pulmonary functions all play important roles in determining the patient's readiness to be discharged from the hospital. A disposition decision may be made if cDS exceeds a specified threshold or falls within a specified range.

In some examples, the health status analyzer circuit 400 may be coupled to a therapy circuit that is configured to deliver a therapy to the patient. The therapy may be delivered in response to one or more of the stability indicator, the health status indicator, or the patient disposition decision satisfying specified condition, such as falling within a specified value range. Examples of the therapy may include electrostimulation therapy or drug therapy, among others.

Figure 5:
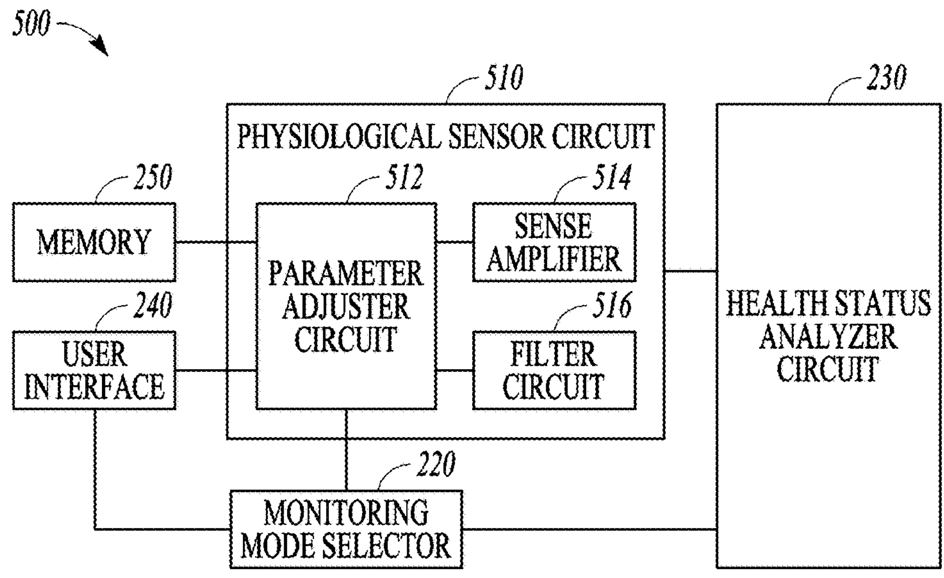
FIG. 5 illustrates generally another example of a patient monitoring system.

FIG. 5 illustrates generally another example of a patient monitoring system 500, which may be an embodiment of the patient monitoring system 200 as illustrated in FIG. 2. The patient monitoring system 500 may include one or more of a physiological sensor circuit 510, a monitoring mode selector 220, a health status analyzer circuit 230, a user interface 240, and a memory 250. The physiological sensor circuit 510, which is an embodiment of the physiological sensor circuit 210, may include a parameter adjuster circuit 512, a sense amplifier circuit 514, and a filter circuit 516. The sense amplifier circuit 514 may include a sampling circuit for sampling a sensed physiological signal at a specified sampling rate, and an analog-to-digital converter (ADC) for digitizing the sensed physiological signal at a specified ADC resolution. The filter circuit 516 may perform filtering of the physiological signal using one or more analog or digital filters each having specified filter coefficients that determine the cutoff frequencies and passband or stopband characteristics.

The parameter adjuster circuit 512, coupled to the sense amplifier circuit 514 and the filter circuit 516, may adjust one or more parameters such as the ADC resolution, sampling rate, or filter coefficients. As illustrated in FIG. 5, the parameter adjuster circuit 512 may be coupled to the monitoring mode selector 220 and the memory 250. Signal processing parameters associated with signal sampling, digitization, or filtering corresponding to different patient monitoring modes may be stored in the memory 250 such as in a form of look-up table, association map, or other data structures. The parameter adjuster circuit 512 may receive from the monitoring mode selector 220 a selected monitoring mode, and determine the corresponding signal processing parameters according to the look-up table or the association map stored in the memory 250. The parameter adjuster circuit 512 may also be coupled to the user interface 240 to receive user command such as for confirming or modifying one or more of the signal processing parameters. In an example, the sampling rate may be changed from 200 Hz in one monitoring mode to 100 Hz in another selected monitoring mode. In another example, the sampling rate may be changed from 100 times a day in one monitoring mode to 20 times a day in another selected monitoring mode.

In an example, in response to a selection of the in-hospital monitoring mode, the sense amplifier circuit 514 may sense the one or more physiological signals using the sampling rate determined according to a change or a rate of change of the one or more physiological signals within a specified time period prior to hospitalization. For example, if a physiological signal or a signal metric generated therefrom changes substantially during a pre-hospitalization monitoring mode (e.g., signal change or rate of change over a specified time prior to patient's admission to a hospital falls below a specified threshold), then the signal or the signal metric may be used for monitoring patient health status during the in-hospital monitoring mode. In an example, the sampling rate of a physiological signal during in-hospital monitoring mode may be proportional to the pre-hospitalization change or the rate of change of the signal, such that a lower sampling rate may be applied to signals that demonstrate more profound pre-hospitalization signal change. A substantial change or rate of change in signal strength may indicate a higher sensitivity of the signal to the change of patient's health status, such that the patient health status change may be more easily detected using more sensitive sensors. A lower sampling rate may reduce the data volume and saves memory space without impairing the sensitivity of detecting the change of patient health status. In another example, the sampling rate may be inversely proportional to the pre-hospitalization signal change or the rate of change, such that a higher sampling rate may be applied to signals that demonstrate more profound pre-hospitalization signal change. A substantial change or rate of change in signal strength may indicate a higher reliability of the signal for detecting patient's response to in-hospital therapies. A higher sampling rate may ensure a reliable and accurate detection of the change of patient health status. The physiological sensor circuit 510 may generate from the processed physiological signals one or more signal metrics, which may be used by the health status analyzer circuit 230 for analyzing patient health status and generating the patient disposition decision.

Figure 6:
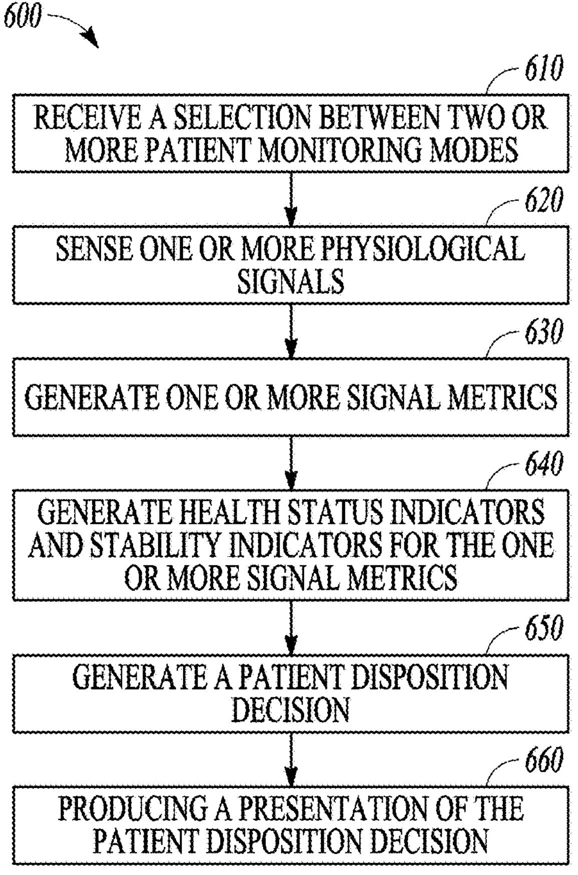
FIG. 6 illustrates generally an example of a method for monitoring a patient using a patient monitoring system.

FIG. 6 illustrates generally an example of a method 600 for monitoring a patient using a patient monitoring system, such as the patient monitoring systems 200 or 400 respectively illustrated in FIGS. 2 and 4. The method 600 may be implemented and executable in an ambulatory medical device (AMD) (including, for example, an implantable or wearable medical device), a programmer for programming the AMD, a patient management system communicating with the AMD, or distributed between the AMD and an external system. In an example, the method 600 may be performed by the patient monitoring system 200, or any modifications thereof.

The method 600 may begin at step 610, by selection between two or more patient monitoring modes, which may include a pre-hospitalization mode ($M_{PreH}$), an in-hospital monitoring mode ($M_H$), or a post-discharge monitoring mode ($M_{PostH}$). The $M_{PreH}$ may be used before the patient is admitted to a hospital. The $M_H$ may be used when patient is being hospitalized. The $M_{PostH}$ may be used when the patient has been discharged from the hospital. The monitoring mode may be selected by a user, such as a clinician, via a user input device such as coupled to the user interface 240 as illustrated in FIG. 2.

At 620, one or more physiological signals may be sensed, such as by using respective physiologic sensors. The physiological signals may be indicative of intrinsic physiologic activity or evoked response to stimulation or other external perturbation. Examples of the physiological signals may include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, central venous pH value, a heart sound (HS) signal, a posture signal, a physical activity signal, or a respiration signal, among others.

The physiological signals may be processed, including amplification, digitization, filtering, or other signal conditioning operations. In an example, parameters used for processing the physiological signals, such as sampling frequency, analog-to-digital conversion resolution, or filter coefficients may be determined based on the selected monitoring mode. In an example, during the in-hospital monitoring mode, a physiological signal may be sensed using a sampling rate determined according to a change or a rate of change of the physiological signal within a specified time period prior to hospitalization. For example, if a physiological signal or a signal metric generated therefrom changes substantially during a pre-hospitalization monitoring mode (e.g., signal change or rate of change over a specified time prior to patient's admission to a hospital falls below a specified threshold), then the signal or the signal metric may be used for monitoring patient health status during the in-hospital monitoring mode. In an example, the sampling rate of a physiological signal during in-hospital monitoring mode may be proportional to the pre-hospitalization change or the rate of change of the signal. In another example, the sampling rate may be inversely proportional to the pre-hospitalization signal change or the rate of change. In an example, the methods for adjusting the parameters such as the sampling frequency, analog-to-digital conversion resolution, or filter coefficients may be implemented in and executed by the physiological sensor circuit 510 as illustrated in FIG. 5, or any modification thereof.

At 630, one or more signal metrics may be generated from the processed one or more physiological signals. The signal metrics may be statistical or morphological features extracted from the physiological signals, and may indicate the patient's health status due to patient's disease progression, treatments, change in medication, or change in posture or activity levels, among others. Examples of the signal metrics may heart rate, heart rate variability, cardiac activation timings, morphological features from the ECG or EGM, impedance magnitude within a specified frequency range, intensities or timings of S1, S2, S3, or S4 heart sounds, systolic blood pressure, diastolic blood pressure, mean arterial pressure, or timing of a pressure metric with respect to a fiducial point, among others.

In some examples, a subset of mode-specific signal metrics may be selected from the one or more signal metrics generated at 630 corresponding to a particular monitoring mode. The correspondence between the monitoring mode and the mode-specific signal metrics may be established and stored such as in the memory 250. The mode-specific signal metrics for the respective patient monitoring mode may be chosen based on information about the ambient environment in which a physiological sensor is used, patient physical or health condition, responsiveness of a physiologic sensor to a particular type of therapy, or sensitivity of a signal metric to progression of patient health status, among others. The signal metrics associated with one monitoring mode may be different from the signal metrics associated with another monitoring mode. In an example, at least one signal metric associated with one monitoring mode is not associated with another monitoring mode. In an example, at least one signal metric may be shared by two different patient monitoring modes. In some examples, a signal metrics associated with a first monitoring mode and another signal metric associated with a second monitoring mode, although not identical from each other, may be generated from the a physiological signal sensed from the same physiological sensor At 640, respective health status indicators and respective stability indicators may be generated for the one or more signal metrics. The health status indicators indicate patient health status, and the stability indicators indicate stability of the patient health status. A health status indicator corresponding to a signal metric X, may be computed as a relative difference ΔX between X respective reference level ($X_{Ref}$). The reference level $X_{Ref}$ may be determined as a baseline value of X under a particular monitoring mode that is different than the present monitoring mode. In an example, the reference $X_{Ref}$ may be a pre-hospitalization baseline determined as a mean, median, or other central tendency index of multiple historical measurements of X during a pre-hospitalization period when the patient is free of heart failure decompensation or other target events. In another example, the reference $X_{Ref}$ may be an in-hospital baseline determined over a specified in-hospital period when the patient is deemed to be recovered from the target disease and remains stable over a specified period of time. The relative difference (ΔX) between X and $X_{Ref}$ may be computed as a deviation $\Delta X = X - X_{Ref}$, or alternatively as percentage change $\Delta X = (X - X_{Ref})/X_{Ref}$. The relative difference ΔX may be compared to a threshold or a specified range to provide the health status indicator.

The health status indicator may alternatively be determined based on a comparison between a change or a rate of change of a signal metric during a first monitoring mode, and a change or a rate of change of the signal metric during a different second monitoring mode. For example, when a patient is being hospitalized for worsening heart failure, a change or rate of change of the signal metric X during an in-hospital period of time may be determined and compared to a corresponding change or rate of change of the same signal metric during a pre-hospitalization period leading up to the hospitalization. A health status indicator may be generated if the change or rate of change of the signal metric during the in-hospital monitoring mode falls within a specified margin of the change or rate of change of X during the pre-hospitalization monitoring mode.

The stability indicator may include variability of one or more mode-specific signal metrics within a specified time period during a patient monitoring mode. Examples of the variability may include a range, a quartile range, a percentile range, a standard deviation, a variance, a coefficient of variance, a skewness or histogram, or a measure of dispersion, among others. In an example, the physiological signals may be filtered such as to remove or attenuate circadian rhythm in the signals, such that the calculated variability would be less affected by the circadian variation of the physiological signal.

At 650, a patient disposition decision may be generated using at least some of the health status indicators and the stability indicators corresponding to the one or more signal metrics $\{X(i)\}=\{X(1), X(2), \ldots, X(N)\}$ selected for a particular monitoring mode. The patient disposition decision may indicate patient readiness for discharge from, or a risk of admission or readmission to a hospital. In an example, for each signal metric X(i) a respective disposition score DS(i) may be generated based on the corresponding health status indicator (such as the relative difference ΔX(i)) and the corresponding stability indicator (such as the variability measure var(X(i))), such as the disposition score $DS_{\|S3\|}$ shown in Equation (1) above. The disposition score DS(i) may indicate a risk associated with patient disposition based on the evidence of the signal metric X(i). Using the stability indicator may reduce the likelihood of improper patient disposition, such as premature patient discharge or unnecessary rehospitalization in certain patients, such that the resulting patient disposition decision may provide more accurate and reliable assessment of patient health status such as a progression of heart failure.

A composite disposition score cDS may then be computed as a combination of the {DS(i)} corresponding to the signal metrics {X(i)}. While an individual DS(i) indicates a risk associated with patient disposition solely based on the evidence provided by the signal metric X(i), the composite disposition score cDS may provide a comprehensive assessment of the risk associated with patient disposition. In an example, the cDS may be a linear weighted combination of the {DS(i)}, such as shown in Equation (2) above. The weight functions applied to the DS(i) may be determined based on signal use or signal characteristics of the corresponding signal metric X(i) during a particular patient monitoring mode. For example, if a signal metric ||S3|| is used prior to patient hospitalization and demonstrates more profound change during a time period leading to an event of HF decompensation and patient hospitalization than another signal metric of rapid shallow breathing index (RSBI), then during the in-hospital monitoring, the weight applied to $DS_{\|S3\|}$ may be greater than the weight applied to $DS_{\|RSBI\|}$. In another example, the cDS may be computed as a nonlinear combination of the {DS(i)}, such as by using a decision tree, a neural network, a fuzzy-logic model, or a multivariate regression model, among others. The patient disposition decision may then be generated if the cDS exceeds a threshold value or falling within a specified range.

At 660, a human-perceptible presentation of the patient disposition decision may be produced and presented in a display such as in the user interface 240. Other information may alternatively or additionally be presented, including the physiological signals, the signals metrics generated from the physiological signals, heath status indicators and stability indicators associated with the signal metrics, device status, selectable patient monitoring modes, or the current selection of the patient monitoring mode, among others. The information may be presented in a table, a chart, a diagram, or any other types of textual, tabular, or graphical presentation formats, for displaying to a system user. The presentation of the output information may include audio or other human-perceptible media format to alert the system user of a transition from one patient monitoring mode to another different patient monitoring mode.

In some examples, the patient disposition decision may be used for automatically switching the present patient monitoring mode to another different monitoring mode. Based on a state machine such as that illustrated in FIG. 3 and the information about the present patient monitoring mode, the patient disposition decision may be used to trigger the monitoring mode switch. For example, a transition from the pre-hospitalization monitoring mode to the in-hospital monitoring mode may be established in response to a hospitalization readiness decision, a transition from the in-hospital monitoring mode to the post-discharge monitoring mode may be established in response to a discharge readiness decision, or a transition from the post-discharge monitoring mode to the in-hospital monitoring mode may be established in response to a readmission readiness decision.

In some examples, the patient monitoring system 200 may additionally include delivering a therapy to the patient such as in response to one or more of the stability indicator, the health status indicator, or the patient disposition decision. Examples of the therapy may include electrostimulation therapy delivered to the heart, a nerve tissue, or other target tissues in response to the detection of the target physiological event, or drug therapy including delivering drug to a tissue or organ. In some examples, the stability indicator, the health status indicator, or the patient disposition decision may be used to modify an existing therapy, such as adjusting a stimulation parameter or drug dosage.

Figure 7:
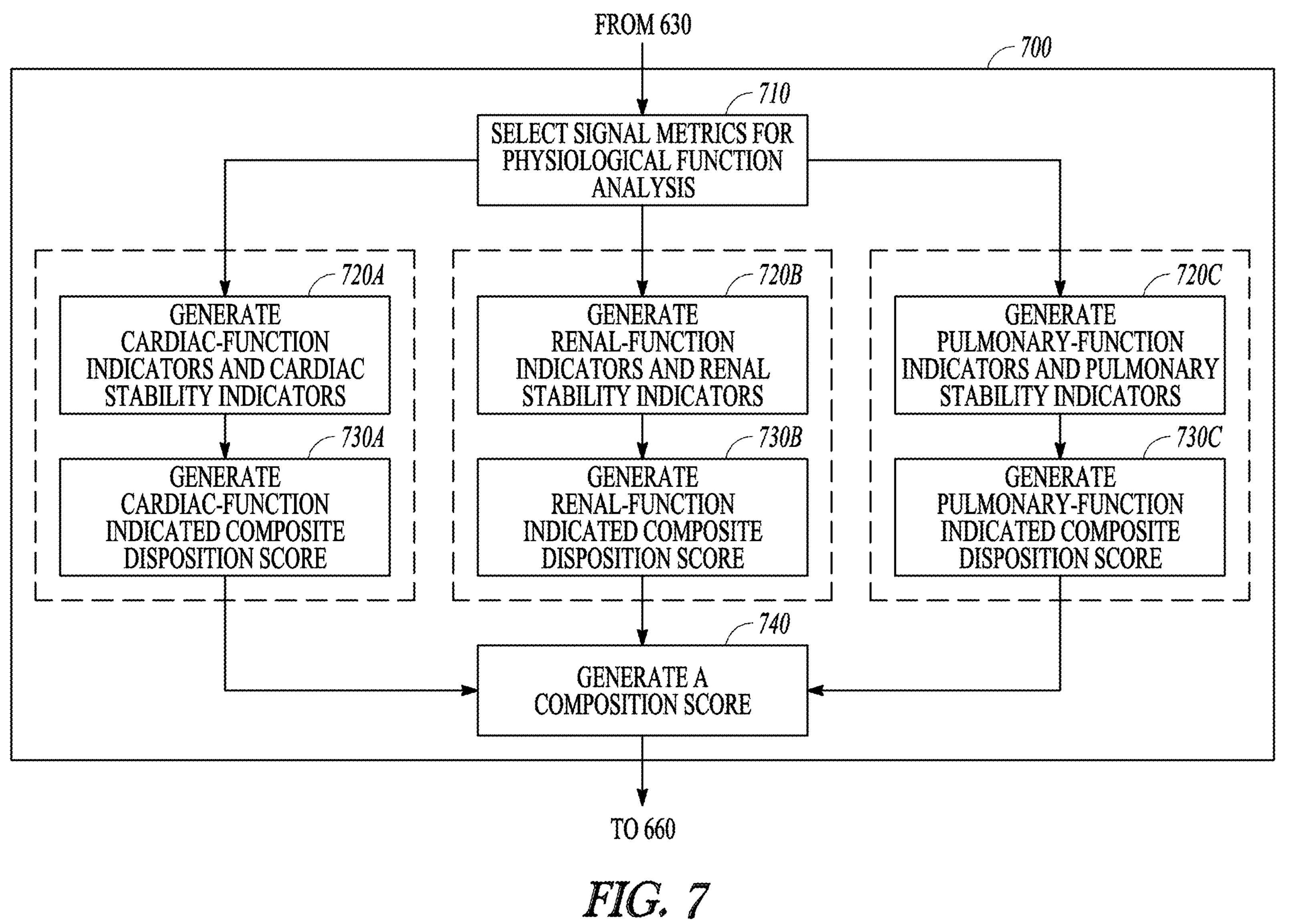
FIG. 7 illustrates generally an example of a method for generating a patient disposition decision based on physiological function analysis.

FIG. 7 illustrates generally an example of a method 700 for generating a patient disposition decision based on physiological function analysis. The method 700, which may be a specific embodiment of the steps of 640 and 650 of FIG. 6 for generating the status indicators, the stability indicators, and the dispositions decision, may be implemented in and executed by the health status analyzer circuit 400, or any modification thereof.

At 710, from the one or more signal metrics produced at 630 one or more mode-specific signal metrics may be selected respectively for analyzing two or more physiological functions, such as cardiac function, renal function, or pulmonary function, among others. The signal metrics selected for one physiological function analysis may be different from the signal metrics selected for another physiological function analysis such as by at least one signal metric. In an example, a signal metric may be selected for two or more physiological function analyzers. Examples of signal metrics ($\{X_C(i)\}$ for cardiac function analysis may include heart rate, heart rate variability, morphological feature extracted from a ECG or an electrogram, intrathoracic impedance, pulmonary arterial pressure, activity level, posture, S1 heart sound strength, S3 heart sound strength, systolic timing interval, or pre-ejection and ejection time, ventricular pressure, or pulmonary arterial pressure, among others. Examples of signal metrics ($\{X_R(j)\}$ for renal function analysis may include creatinine level, body urea nitrogen (BUN) level, BUN/creatinine ratio, or glomerular filtration rate (GFR), among others. Examples of signal metrics ($\{X_P(k)\}$=for pulmonary function analysis may include respiration rate, rapid shallow breathing index, tidal volume, thoracic impedance, heart sounds, heart rates, or pulmonary arterial pressure, among others.

The selected signal metrics $\{X_C(i)\}$ may then be used to generate respective cardiac function indicators and cardiac stability indicators at 720A. Likewise, the selected signal metrics $\{X_R(j)\}$ may be used to generate respective renal function indicators and renal stability indicators at 720B, and selected signal metrics $\{X_P(k)\}$ may be used to generate respective pulmonary function indicators and pulmonary stability indicators at 720C. Similar to status indicator and stability indicator generation at 640 of FIG. 6, a particular physiological function indicator associated with $X_C(i)$, $X_R(j)$, or $X_P(k)$) may be computed as a relative difference between the signal metric and a reference level, and a cardiac stability indicator may be computed as a variability of the signal metric over a specified period of time during a particular patient monitoring mode.

At 730A, a cardiac-function indicated composite disposition score $cDS_C$ may be computed based on the cardiac function indicators and cardiac stability indicators. In an example, the $cDS_C$ may be a combination of disposition scores corresponding to some or all of the signal metrics $\{X_C(i)\}$. Likewise, a renal-function indicated composite disposition score $cDS_R$ may be computed at 730B using a combination of disposition scores corresponding to some or all of the signal metrics $\{X_R(j)\}$, and a pulmonary-function indicated composite disposition score $cDS_P$ may be computed at 730C using a combination of disposition scores corresponding to some or all of the signal metrics $\{X_P(k)\}$. In an example, the combination may be a linear weighted combination, such as shown in Equation (3).

At 740, some or all of the physiological function-indicated composite disposition scores, such as the $cDS_C$, the $cDS_R$, and the $cDS_P$, may be combined to generate the composite disposition score cDS, such as a weighted combination of the $cDS_C$, the $cDS_R$, and the $cDS_P$ as shown in Equation (4). A disposition decision may be made if cDS exceeds a specified threshold or falls within a specified range. In another example, a patient disposition may be generated if the $cDS_C$, the $cDS_R$, and the $cDS_P$ each exceeds respectively specified threshold or falls within a respectively specified range. The patient disposition decision, among other information, may be presented to a system user at 660.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A system for monitoring a patient, the system comprising:

a sensor circuit configured to receive physiological information from the patient;

a processor circuit configured to:

for each of a plurality of risk categories, generate (i) a progression indicator indicating an amount of change in a portion of the physiological information associated with a corresponding risk category from a reference level, and (ii) a stability indicator indicating stability of the portion of the physiological information associated with the corresponding risk category over time, and determine a risk-indicated disposition score based on the progression indicator and the stability indicator; and based on the risk-indicated disposition scores respectively determined for the plurality of risk categories, generate a disposition indicator indicating a cause of patient disposition; and an output unit configured to output the disposition indicator to a user or a process.

2. The system of claim 1, wherein the plurality of risk categories include distinct first and second risk categories each selected from the group consisting of a cardiac risk, a pulmonary risk, and a renal risk, wherein the processor circuit is configured to generate the disposition indicator indicating the patient disposition attributable to one of a cardiac cause, a pulmonary cause, or a renal cause.

3. The system of claim 2, wherein the processor circuit is configured to:

determine a first risk-indicated disposition score for the first risk category using progression indicator and stability indicator generated from a first portion of the physiological information; and determine a second risk-indicated disposition score for the second risk category using progression indicator and stability indicator generated from a second portion of the physiological information different from the first portion.

4. The system of claim 1, wherein the physiological information include one or more physiological signals, wherein the processor circuit is configured to generate signal metrics from the one or more physiological signals, and to determine the risk-indicated disposition score using progression indicators and the stability indicators respectively determined for each of the signal metrics.

5. The system of claim 4, wherein the processor circuit is configured to determine the risk-indicated disposition score using a combination of metric-specific disposition scores respectively determined for each of the signal metrics.

6. The system of claim 5, wherein the combination includes a weighted combination of the metric-specific disposition scores.

7. The system of claim 4, wherein the disposition indicator indicates a cause of patient hospitalization, wherein the processor circuit is configured to generate, for each of the plurality of risk categories, the progression indicator based on the amount of change of the signal metrics from respective pre-hospitalization baseline values.

8. The system of claim 4, wherein the disposition indicator indicates a cause of patient discharge from a hospital, wherein the processor circuit is configured to generate, for each of the plurality of risk categories, the progression indicator based on the amount of change of the signal metrics from respective pre-discharge baseline values.

9. The system of claim 4, wherein the processor circuit is configured to generate the signal metrics in accordance with a patient monitoring mode, the patient monitoring mode including one of a pre-hospitalization mode, an in-hospital monitoring mode, or a post-discharge monitoring mode.

10. The system of claim 9, wherein the processor circuit is configured to determine first signal metrics for a first patient monitoring mode, and to determine second signal metrics different from the first signal metrics for a second patient monitoring mode.

11. The system of claim 1, wherein the processor circuit is configured to generate a composite disposition score using a combination of the risk-indicated disposition scores.

12. A system for monitoring a patient's health status, the system comprising:

a sensor circuit configured to receive physiological information from the patient; and a processor circuit configured to:

determine a cardiac risk-indicated disposition score using (i) a first progression indicator indicating an amount of change in a first portion of the physiological information associated with a cardiac risk, and (ii) a first stability indicator indicating stability of the first portion of the physiological information over time;

determine a pulmonary risk-indicated disposition score using (i) a second progression indicator indicating an amount of change in a second portion of the physiological information associated with a pulmonary risk, and (ii) a second stability indicator indicating stability of the second portion of the physiological information over time;

determine a renal risk-indicated disposition score using (i) a third progression indicator indicating an amount of change in a third portion of the physiological information associated with a renal risk, and (ii) a third stability indicator indicating stability of the third portion of the physiological information over time; and based on the cardiac risk-indicated disposition score, the pulmonary risk-indicated disposition score, and the renal risk-indicated disposition score, generate a disposition indicator indicating patient disposition attributable to one of a cardiac cause, a pulmonary cause, or a renal cause.

13. The system of claim 12, wherein the physiological information includes one or more physiological signals, wherein the processor circuit is configured to:

generate cardiac signal metrics, pulmonary signal metrics, and renal signal metrics from the one or more physiological signals;

determine the cardiac risk-indicated disposition score using first progression indicators and first stability indicators respectively determined for each of the cardiac signal metrics;

determine the pulmonary risk-indicated disposition score using second progression indicators and second stability indicators respectively determined for each of the pulmonary signal metrics; and determine the renal risk-indicated disposition score using third progression indicators and third stability indicators respectively determined for each of the renal signal metrics.

14. A method for monitoring a patient using a monitor system, the method comprising:

receiving physiological information sensed from the patient;

for each of a plurality of risk categories, generating (i) a progression indicator indicating an amount of change in a portion of the physiological information associated with a corresponding risk category from a reference level, and (ii) a stability indicator indicating stability of the portion of the physiological information associated with the corresponding risk category over time using a processor circuit, determining a risk-indicated disposition score based on the progression indicator and the stability indicator, using a processor circuit;

based on the risk-indicated disposition scores respectively determined for the plurality of risk categories, generating a disposition indicator indicating a cause of patient disposition; and outputting, via an output unit, the disposition indicator to a user or a process.

15. The method of claim 14, wherein the plurality of risk categories include distinct first and second risk categories each selected from the group consisting of a cardiac risk, a pulmonary risk, and a renal risk, wherein the disposition indicator indicates the patient disposition attributable to one of a cardiac cause, a pulmonary cause, or a renal cause.

16. The method of claim 14, wherein the physiological information include one or more physiological signals, the method further comprising:

generating signal metrics from the one or more physiological signals; and determining the risk-indicated disposition score using progression indicators and stability indicators respectively determined for each of the signal metrics.

17. The method of claim 16, wherein determining the risk-indicated disposition score includes using a weighted combination of metric-specific disposition scores respectively determined for each of the signal metrics.

18. The method of claim 16, wherein the disposition indicator indicates a cause of patient hospitalization, wherein, for each of the plurality of risk categories, generating the progression indicator is based on the amount of change of the signal metrics from respective pre-hospitalization baseline values.

19. The method of claim 16, wherein the disposition indicator indicates a cause of patient discharge from a hospital, wherein, for each of the plurality of risk categories, generating the progression indicator is based on the amount of change of the signal metrics from respective pre-discharge baseline values.

20. The method of claim 14, further comprising generating a composite disposition score using a combination of the risk-indicated disposition scores.

* * * * *